United States Patent [19]

Badylak et al.

[11] Patent Number: 4,902,508

[45] Date of Patent: Feb. 20, 1990

[54] TISSUE GRAFT COMPOSITION

[75] Inventors: Stephen F. Badylak; Leslie A. Geddes, both of West Lafayette; Gary Lantz, Lafayette; Arthur C. Coffey, Indianapolis, all of Ind.

[73] Assignee: Purdue Research Foundation, West Lafayette, Ind.

[21] Appl. No.: 217,299

[22] Filed: Jul. 11, 1988

[51] Int. Cl.$^4$ .............................................. A65R 35/38
[52] U.S. Cl. ......................................... 424/95; 623/1; 623/11; 623/12
[58] Field of Search ................. 424/95; 623/1, 11, 12; 128/335.5

[56] References Cited

U.S. PATENT DOCUMENTS 3,562,820  2/1971  Braun ...................................... 623/1
4,502,159  3/1985  Woodroof et al. ...................... 623/1

OTHER PUBLICATIONS

Mitchell-Heggs, Francis & H. Guy Radcliffe Drew, *The Instruments of Surgery*, William Heinemann, London, 1963, p. 87.

"Experimental Replacement of Superior Vena Cava", Fraser et al., *Arch. Surg.*, vol. 96, Mar. 1968, pp. 378–385.

"Replacement of Dog's Aorta by Autologous Intestinal Muscle in the Infected Retroperitoneum", Broll et al., *Eur. Surg. Res.*, vol. 18, 1986, pp. 390–396.

"Evaluation of Canine Intestinal Submucosa as a Vascular Substitute", Lawler et al., *The American Journal of Surgery*, vol. 122, Oct. 1971, pp. 517–519.

"Glutaraldehyde Treated Cat Small Bowel as an Arterial Graft", Dagan et al., *Vascular Surgery*, Jul./Aug., 1983, pp. 199–206.

"A Study of Inverted Intestinal Graft in the Major Veins", Matsumoto et al., presented at the Eleventh Annual Meeting of the American College of Angiology, New York, Jun., 1966, pp. 842–850.

"The Fate of the Inverted Segment of Small Bowel Used for the Replacement of Major Veins", Matsumoto et al., *Surgery*, vol. 60, No. 3, Sep. 1966, pp. 739–743.

"Experimental Study of Vascular Graft II. Replacement of Inferior Vena Cava and Abdominal Aorta with the Autogenous Segment of Small Intestinal Submucosa", Egusa, S., *Acta Med. Okayama*, 22, 153–165, (1968).

G. Rotthoff et al., "Aortic Replacement . . . ", 8th Congress of Intn'l. Society of Cardiovascular Surgery, Vienna, Sep. 7–9, 1967.

R. Haring et al., "Long Term Observations . . . Heart Wall Grafts from Small Intestine", Langenbecks Arch. Klin. Chir., 1965, 313:664–8.

G. Rotthoff et al., "Replacement of the Aorta . . . Heterologous Ileum", Bulletin Da La Societe Intn'l de Chirurgie, No. 2, 1969, 256–259.

J. H. Huth, "Replacement of the Abdominal Aorta . . . ", Zentralbl chir 92, (26/2):1817–19, (1967).

G. Rotthoff et al., Langenbecks Archiv. Klin. Chir., 1964, 308, pp. 816–820.

J. H. Huth et al., Thoraxchir. Vask. Chir., 1967, Aug., 15(4):401–7.

H.-P. Bruch et al., Folia Angiologica, vol. 29, (3–5/81), pp. 65–68.

*Primary Examiner*—Johnnie R. Brown
*Assistant Examiner*—Jean C. Witz
*Attorney, Agent, or Firm*—Barnes & Thornburg

[57] ABSTRACT

This invention relates to a method for preparation of a tissue graft composition from a segment of small intestine. A tissue graft composition is described which comprises the tunica submucosa of a segment of small intestine of a warm-blooded vertebrate wherein the tunica submucosa is delaminated from the tunica muscularis and at least the luminal portion of the tunica mucosa. The tissue graft composition has been shown to have excellent mechanical characteristics, as well as non-allergenicity and non-thrombogenicity in applications as vascular autografts, vascular allografts, and vascular heterografts.

4 Claims, 1 Drawing Sheet

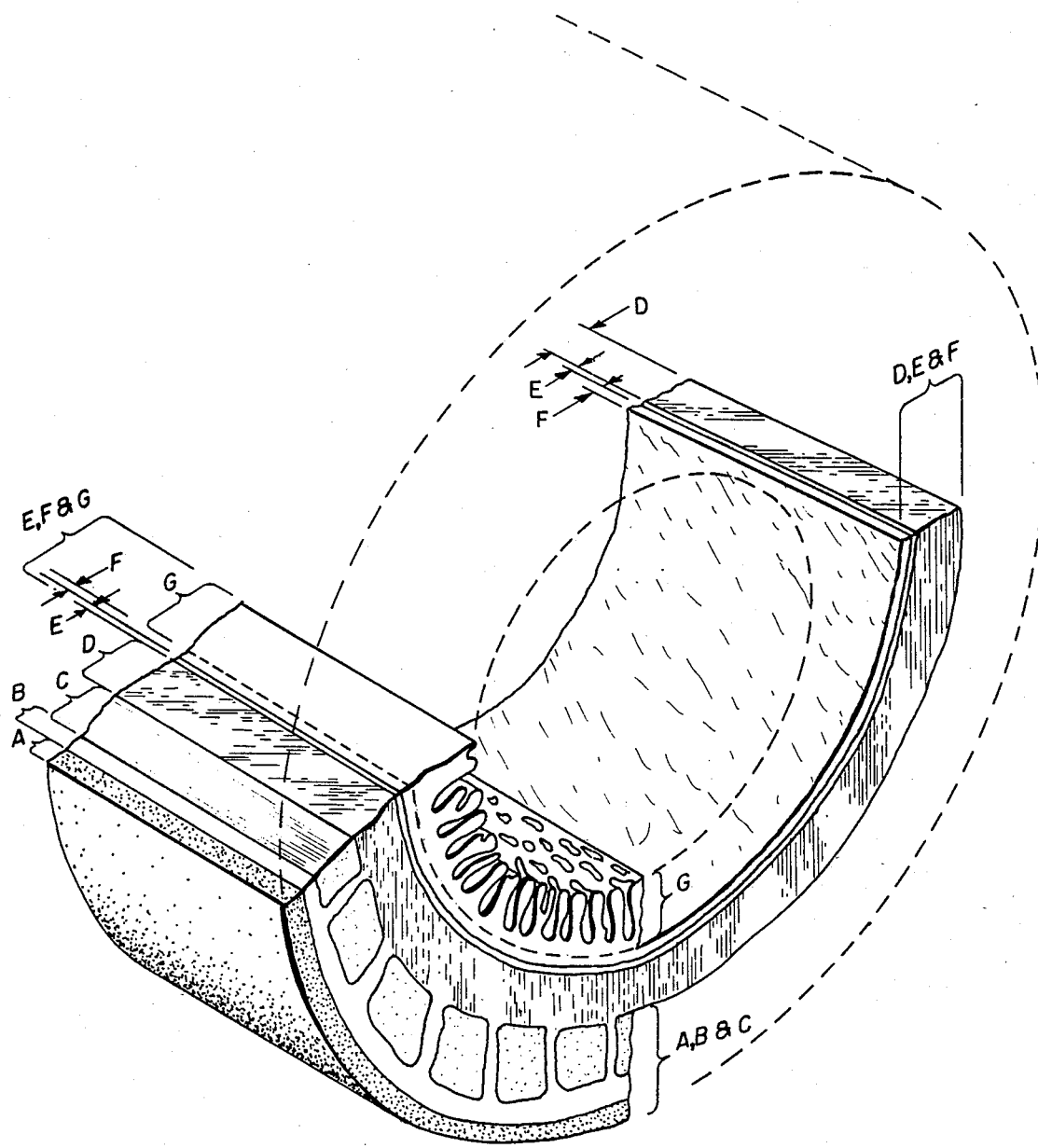

TISSUE GRAFT COMPOSITION

This invention relates to a novel tissue graft composition exhibiting strength, patency, infection resistance, non-immunogenicity, non-thombogenicity, and resistance to aneurysm formation surpassing many synthetic graft materials. More particularly, this invention is directed to tissue graft compositions comprising the submucosal and basilar mucosal portions of the small intestine and to methods for preparation and use of such compositions.

BACKGROUND OF THE INVENTION

Tissue graft materials have today attained considerable clinical and economic significance. It is estimated that in 1986 $130 million was spent for vascular grafts alone, not including coronary artery bypass grafts. Yet success rates for vascular graft procedures pale in comparison to those of most other surgical procedures. For example, a 5-year cumulative patency of 50% is considered excellent for small diameter vascular grafts. Such low success rates result, in large part, from one or more physical or functional deficiencies in the graft materials currently in clinical use.

Identification of materials suitable for tissue grafts is particularly difficult because such materials must possess a variety of disparate properties. For example, vascular graft materials must not only exhibit mechanical stability under continuous stress, but they also must have porosity adequate for capillarization, compliance similar to that of the host tissue, and high negative Zeta potentials (so as to be nonthrombogenic). Further they should be non-allergenic, non-carcinogenic, and preferably inexpensive to fabricate.

Few, if any, tissue graft materials possess all of the desirable properties. Literature reports of research and development in the area of vascular grafts reflect a significant ongoing effort to overcome the shortcomings common to currently known graft materials.

Both synthetic and autogenous materials have been used for vascular grafts. Among synthetics, expanded polytetrafluoroethylene (PTFE) is a commonly used vascular graft material, particularly for small vessel bypass surgeries. However, expanded PTFE grafts are susceptible to neointimal hyperplasia and late graft thrombosis (e.g., 6-year patency rates of approximately 50% for femoropopliteal bypasses). PTFE grafts are reported to have even lower success rates when used in the venous circulation.

Another synthetic material - Dacron ® - is often used for large diameter vascular graft procedures (e.g., infrarenal aortic grafts). Knitted Dacron ®, however, has a relatively high porosity and must be preclotted prior to implantation to avoid extensive hemorrhage. This preclotting procedure is not always practical or successful. Woven Dacron ®, while less porous, demonstrates a compliance of only 20% of that found in a normal aorta. Finally, Dacron ® grafts perform poorly in small diameter arteries or veins where blood flow is relatively slow.

One of the more significant problems associated with use of synthetics as tissue graft materials is the fact that synthetic materials have low infection resistance. Infection rates following synthetic graft implantation are associated with a 66% mortality rate. Synthetic materials tend to harbor microorganisms in their interstices and, when contaminated, are extremely refractory to antibacterial therapy. Explantation of infected synthetic grafts is virtually inevitable.

More recently researchers have reported preparation of synthetic skin and blood vessel equivalents utilizing living human cells. See U.S. Pat. Nos. 4,604,346, 4,546,500, 4,539,716, 4,485,097, and 4,485,096.

Among autogenous materials, the saphenous vein, the human umbilical vein, the inverted small intestine, and the radial artery have all been used, but each of these materials has also exhibited significant shortcomings. The saphenous vein may be of an inappropriate size for certain procedures or may be unavailable because of damage by disease. In addition, the saphenous vein may have unacceptable varicosities and suffers from accelerated atherogenesis following "arteriolization." Both the umbilical grafts and the inverted small intestine grafts are plagued by early thrombosis and late aneurysm formation. Finally, the radial artery is of limited utility because it is difficult to harvest and may deteriorate after graft implantation.

It is therefore an object of this invention to provide a tissue graft material which does not exhibit many of the shortcomings associated with many graft materials now being used clinically.

Another object of this invention is to provide a method for preparing a novel tissue graft material from a section of small intestine.

Still another object of this invention is to provide a method for use of a novel multi-purpose tissue graft material in autografting, allografting and heterografting applications.

Yet a further object of this invention is to provide a method for using a novel tissue graft composition for blood vessel replacement.

BRIEF DESCRIPTION OF THE DRAWING

FIG. 1 is a cross-sectional view of a section of the small intestine.

DETAILED DESCRIPTION OF THE INVENTION

This invention is directed to a tissue graft composition comprising primarily the tunica submucosa of a segment of small intestine of a warm-blooded vertebrate. The tunica submucosa is delaminated from the tunica muscularis and at least the luminal portion of the tunica mucosa of the section of small intestine. While the present tissue graft composition has been shown to have excellent functional characteristics in applications as vascular autografts and vascular allografts, it is anticipated that tissue graft compositions of this invention will find wide use even as heterografts in both vascular and in other tissue graft applications. Applicants have discovered that the subject tissue graft composition exhibits multiple physical and biological characteristics that renders it particularly adapted for tissue graft applications.

In a preferred embodiment of this invention, the tissue graft material comprises submucosa tissue and basilar mucosa tissue delaminated from a segment of the small intestine, more preferably the jejunum, a division of the small intestine extending between the duodenum and the ileum. The small intestine, prior to its manipulation (delamination) to yield graft material in accordance with this invention, is made up of a number of discrete tissue layers. FIG. 1 provides a cross-sectional view of the small intestine showing its discrete tissue layers labeled A through G (outer to inner, respectively)

which collectively define the intestinal wall. The outermost tissue layer A represents the mesenteric tissues. The mesenteric tissues are depicted as a distinct layer for illustrative purposes only. Ordinarily such tissues do not appear as a discrete layer, but rather appear as discontinuous tissue segments. Layers B and C represent the tunica serosa and the tunica muscularis, respectively. Layer D, the tunica submucosa, is a dense, irregular collagenous connective tissue often harboring numerous mast cells. Heparin derived from these mast cells is probably at least partially responsible for the lack of early thrombogenicity of the graft material.

Layers E, F, and G collectively represent the so-called tunica mucosa. Layer E is a layer of smooth muscle cells known as the lamina muscularis mucosa. Layer F, the stratum compactum, consists of acellular collagen and elastin fibers. Layer G consists of the lamina epithelialis mucosa and its lamina propria, which together and arranged in villous processes, a series of finger-like outgrowths of the mucous membrane.

Following the below-detailed manipulation of the intestinal tissue segment to prepare the graft material of this invention, histologic examination reveals that the lamina epithelialis mucosa and its lamina propria have been removed, as have the tunica muscularis and the tunica serosa. The preferred graft material of this invention thus comprises the tunica submucosa D, along with basilar portions of the tunica mucosa, particularly the lamina muscularis mucosa E and the stratum compactum F. Those layers collectively are referred to hereinafter as the Small Intestine Submucosa ("SIS")

A SIS autograft in accordance this invention can be prepared, for example, by first resecting a segment of autogeneous proximal jejunum following a midline laparotomy incision. The resected segment of jejunum is then wrapped in surgical sponges which have been soaked in physiologic saline. Upon completion of the intestinal anastomosis, the excised intestinal segment is prepared in accordance with the hereinafter described method of this invention for use as a tissue graft material. Similarly, allografts are prepared from intestinal tissue removed from organ/tissue donors of the same species. Heterografts can be prepared, for example, from feline, porcine, or bovine intestinal tissue retrieved from euthanized animals at slaughterhouse operations. To date, but minimal morphological differences have been found in intestinal tissues from different species. Indeed, the histologic appearance of human graft tissue in accordance with this invention was found to be almost identical to that of the dog. The only recognizable morphologic difference was a sightly less dense stratum compactum in the human tissue.

The tissue graft material of this invention is prepared by abrading intestinal tissue to remove the outer layers including both the tunica serosa and the tunica muscularis (layers B and C in FIG. 1) and the inner layers including at least the luminal portion (layer G) of the tunica mucosa (layers E through G in FIG. 1). Under conditions of mild abrasion the tunica mucosa is delaminated between the stratum compactum (layer F) and the lamina propria of layer G. More particularly, following removal of any mesenteric tissues from the intestinal segment utilizing, for example, Adson-Brown forceps and Metzenbaum scissors, the tunica serosa and the tunica muscularis (the outer tissue layers) are delaminated from the intestinal segment by abrasion using a longitudinal wiping motion with a scalpel handle and moistened gauze. Following eversion of the intestinal segment, the luminal portion of the tunica mucosa is delaminated from the underlying tissue using the same wiping motion. Care is taken to prevent perforation of the submucosa. Also, any tissue "tags" from the delaminated layers remaining on the graft surface are removed. Optionally, the intestinal segment may be everted first, then stripped of the luminal layers, then reinserted to its original orientation for removal of the tunica serosa and the tunica muscularis. The graft material is a whitish, translucent tube of tissue approximately 0.1 mm thick, typically consisting of the tunica submucosa with the attached lamina muscularis mucosa and stratum compactum. For vascular graft preparation, the prepared graft is everted to its original orientation so that the stratum compactum serves as the luminal surface of the graft.

The prepared graft material is typically rinsed with saline and placed in a 10% neomycin sulfate solution for approximately 20 minutes, after which time the graft material is ready for use. The grafts are applied using routine surgical procedures commonly employed for tissue graft applications. For use in non-vascular tissue graft applications, the tubular graft material can be cut longitudinally and rolled out to form a "patch" of tissue. Indeed, the entire tissue delamination procedure described above can be carried out on "patches" of intestinal tissue prepared by cutting the intestinal segment longitudinally and "unrolling" it to form a pre-graft patch. The prepared graft tissue patches can be utilized, for example, as a skin graft material or for repair of other body tissue defects lending themselves to surgical application of a tissue graft patch having the physical and functional characteristics of the present graft composition.

For use in vascular grafts, the diameter of the graft should be about the same as the diameter of the recipient blood vessel. This is accomplished by manipulating the tissue graft to define a cylinder having a diameter approximately the same as that of the recipient blood vessel and suturing or otherwise securing the tissue graft longitudinally to form said vascular graft. Thus, for example, a vascular graft can be prepared by selecting a sterile glass rod having an outer diameter equal to that of the recipient blood vessel and introducing the glass rod into the graft lumen. Redundant tissue is then gathered and the desired lumen diameter achieved by suturing along the length of the graft (for example, using two continuous suture lines or a simple interrupted suture line) or by using other art-recognized tissue securing techniques.

Consistent with the objects of this invention, the SIS composition possesses mechanical properties highly desirable for tissue graft materials, including low porosity index, high compliance, and a high burst pressure point. As for porosity, one skilled in the art will appreciate that tissue graft material must be of low enough porosity to prevent intraoperative hemorrhage and yet of high enough porosity to allow extension of a newly-developed vasa vasorum through the graft material to nourish the neointima and luminal surface. Porosity of a graft material is typically measured in terms of ml of water passed per $cm^2 min^{-1}$ at a pressure head of 120 mm Hg. The porosity index of the SIS graft material is 10, much lower than other graft materials currently known in the art. (Woven Dacron®, for example, has a porosity index of 50). Yet despite this low porosity index, SIS is still sufficiently porous to allow neocapillarization to occur within the SIS graft. In vascular graft applications SIS compositions allow for the formation of blood-filled capillaries within the graft wall extending to the luminal surface as early as four days after surgery.

Regarding graft compliance, there has been described in the art the existence of a direct relationship between compliance and patency. Ideally a graft material should be at least as compliant as the tissue it replaces. Longitudinal compliance of the SIS graft material was measured through use of a simple tensile test. An initial gage length was formed with two ink marks 5.0 cm apart. The elongation and applied force were measured as the samples were loaded at a tension rate of 32 cm/cm/min, yielding the following results:

Compliance of SIS graft: 0.045 cm/N per cm of length
  Compliance of normal dog aorta: 0.017 cm/N per cm of length Thus, SIS graft materials actually exhibit compliance greater than that of the normal aorta. This is a significant advance over the prior art in the vascular graft area. All presently available synthetic grafts are 3 to 10 times less compliant than the natural artery and proportionately more prone to thrombosis than the natural artery. The prior art method of compensating for this compliance mismatch is to use a graft material larger in diameter than the adjacent natural artery. This technique, however, has lead to additional problems. Blood velocity is slower through the larger diameter graft segment. Hence, there is less shear stress at the graft wall. Under such conditions, platelet and fibrin deposition and subsequent thrombosis are more likely. In contrast, because the SIS material demonstrates such high compliance, isodiametric SIS grafts can be used without occurrence of such problems.

The present SIS graft material was found to have a burst pressure point well beyond what would be encountered physiologically. A burst pressure test was conducted by attaching a tubular SIS graft segment to two 25 mm diameter cylinders and pressurizing the graft with nitrogen gas at a constant flow rate. Two flow rates were used. At the lower flow rate, pressure initially increased, then dropped off and steadied as the gas outflow through the graft wall equilibrated with the gas inflow. At the higher flow rate, the pressure built up immediately to burst conditions at approximately 400 mm Hg, indicating that the graft material can easily withstand the continuous pulsatile pressures encountered in normal physiological vascular graft usage.

EXAMPLES

Example 1

Small Intestinal Submucosa as a Large Diameter Arterial Graft

A series of experiments have been conducted which tested the ability of three different configurations of small intestine to serve as a vascular graft in the infrarenal aorta of the dog. The first experiment utilized a full thickness, non-inverted segment of jejunum, either with an intact mesenteric neurovascular supply or with a free, isolated segment as the graft material. The intestinal mucosa was the blood-graft interface. All 4 dogs in this experiment died within 18 hours of surgery from thrombosis of the graft segment and hemorrhage from the suture lines.

The second experiment utilized an isolated and inverted segment of jejunum as the graft with the tunica serosa serving as the blood-graft interface. There were 2 dogs in this experiment. The graft in the first dog was thrombosed within 4 hours of surgery, and the second dog died from acute hemorrhage at the proximal anastomosis site 4 days following surgery.

The third experiment tested the use of only a portion of the intestinal wall as the graft material. A free segment of autogenous upper jejunum was harvested from each dog and then the majority of mucosa was removed by bluntly scraping the luminal surface with a scalpel handle. By the same procedure, the serosa and tunica muscularis were then removed. The tissue that remained after this seemingly brutal manipulation of the gut segment was a 100 $\mu$ thick section of submucosa and basilar mucosa. This graft was then placed in the infrarenal aorta of 15 dogs and has been remarkably successful. The results of this third experiment are summarized below.

Thirteen of the 15 dogs maintained patent grafts until the time of euthanasia. Eleven dogs were euthanized at various times after surgery ranging from 4 days until 1 year. The animals showed no signs of graft infection, aneurysm formation, or thrombosis. The graft failure observed in two of the dogs was caused by technical error, including misplacement of metal ligaclips and poor anastomosis technique. Two animals remain alive at the time of this writing and are being monitored for more long term graft patency.

The patency of the grafts was verified by positive contrast radiography within four to seven days after the surgery and every 6 to 8 weeks thereafter. In addition, the graft patency was monitored clinically by observing the presence of a strong femoral pulse and the lack of hind limb edema.

Eleven of the dogs maintaining patent grafts were sacrificed at various post-surgery time intervals (4, 7, 10 and 14 days, and 9, 11, 13, 17, 26, 44, and 52 weeks). Just prior to euthanasia, the animals had an additional angiogram to confirm graft patency and to provide a comparative radiograph for evaluation of graft dilatation, stenosis, and aneurysm formation. All eleven of the animals showed complete patency with no evidence of detrimental luminal changes.

Gross pathologic evaluation of these graft segments showed a glistening luminal surface with haphazardly arranged red and white areas and no evidence of propagating thrombus formation. There was a surrounding firm connective tissue accumulation which was confluent with the graft wall. All specimens examined prior to 6 months after surgery showed no evidence of endothelial cell growth on the surface of the graft. The surface of these grafts were covered with a flat, moderately dense and organized layer of collagen.

Histopathologic examination of the 26, 44 and 52 week specimens showed a flattened, "endothelial-like" cell which partially covered a thin (approximately 500$\mu$) layer of densely organized fibrin. The entire tissue was infiltrated with blood-filled capillaries, and the outer border of the original graft material could not be distinguished from the surrounding connective tissue. Scanning electron microscopic examination of the luminal surface showed a layer of flattened cells, indistinguishable from endothelial cells, with extended "pseudopodia". Transmission electron microscopic evaluation of these graft segments also suggested the presence of an endothelial cell covering of the luminal surface. In addition, the presence of Factor VIII: Related Antigen, detected by immunofluorescent staining, further suggested the endothelial origin of these graft luminal surface cells. The graft material was also tested for endothelial cell presence by testing for the presence of endothelium derived relaxing factor. Acetylcholine was applied to the surface of graft specimens and the effluent collected. The effluent was shown through observation of smooth muscle relaxation in a rat aorta preparation to contain endothelium-derived relaxing factor.

The blood pressure cephalad to, distal to, and within the SIS graft was determined in each of the 10 euthanized dogs. The pressures were identical at all 3 locations in each of the dogs, reflecting a lack of adverse hemodynamic effects arising through use of the SIS graft material.

The following laboratory parameters were measured before surgery, one day after surgery, then at additional times during subsequent months in all dogs: hematocrit, prothrombin time, activated partial thromboplastin time, platelet count, complete blood count, and an abbreviated serum chemistry profile. Results showed all animals to be normal by these laboratory measurements at all times. These animals were given low dose heparin treatment (600 units IV) during the surgical procedure, but were not anticoagulated during the postoperative period. The lack of any changes in the coagulation tests and platelet counts was particularly encouraging in light of the relatively hyperactive coagulation system of the dog compared to man.

Example 2

Small Intestinal Submucosa as a Small Diameter Arterial Graft

This experiment involved the implantation in eighteen dogs of a total of 36 grafts in both the femoral artery and the carotid artery. Thirty-three of the thirty-six grafts remained patent. Identical laboratory measurements were made in these animals as were made in the first study and no abnormalities were observed. In addition, conventional 2-dimensional ultrasound imaging was used to measure patency and cross-sectional vessel diameter.

Pathologic examination of graft tissue from a dog euthanized four days after surgery showed a nonthrombotic luminal surface and a mildly stenotic proximal anastomosis. Histologic examination revealed the early presence of blood-filled capillaries within the graft wall, a potential natural body defense to infection. Five of these dogs remain alive at the time of this writing for further evaluation. The longest surviving dog in the study is now 7 months post-surgery.

Example 3

Small Intestinal Submucosa as a Venous Graft

In this experiment, the SIS graft was placed in the posterior vena cava (analogous to the "inferior" vena cava in man) of two dogs and in the anterior vena cava (analogous to the "superior" vena cava in man) of five dogs. Although the posterior vena cava grafts remained patent for only 11 and 14 days respectively, pathologic examination showed failure of the grafts to be attributable to technical errors in which the inferior anastomosis site was stenotic (8mm in diameter as versus the adjacent 16 mm diameter natural vena cava and proximal graft). Moreover, the luminal surfaces of both grafts were covered with a nonthrombotic "psuedoenthelium" composed of tightly packed fibrin and immature collagenous connective tissue.

The anterior vena cava grafts remained patent until euthanasia of three of the dogs at 7, 14, and 21 days respectively, after surgery. Two of the dogs remain alive at the time of this writing with patent grafts at 7 weeks after surgery. The proximal suture line in all three dogs showed evidence of early thrombosis where a flap of the graft had been inverted and was causing turbulent blood flow, but the remainder of the graft was nonthrombotic. In addition, gross pathologic and histologic examinations revealed that the graft was lined by a glistening, smooth red surface identical in appearance to early grafts studied in previous experiments.

Example 4

Small Intestinal Submucosa as an Arterial Allograft

SIS has been used as a large diameter allograft in the dog aorta. The allografts were constructed in the same manner as those described above for our study of aortic autografts. At the time of this writing the test animals are only 8 weeks post surgery, but they show no signs of graft thrombosis, infection or aneurysm formation (as documented by angiograms).

Example 5

Small Intestinal Submucosa as an Arterial Heterograft

SIS has been used as a heterograft in the dog. A SIS graft of feline origin was prepared in accordance with the procedures hereinbefore described and placed in a dog. At the time of this writing, the test animal was two weeks post-surgery and showing no adverse signs.

We claim:

1. A tissue graft composition comprising the tunica submucosa, the muscularis mucosa and the stratum compactum of the tunical mucosa, of a segment of small intestine of a warm-blooded vertebrate, said tunica submucosa, muscularis mucosa and stratum compactum being delaminated from the tunica muscularis and the luminal portion of the tunica mucosa of said section of small intestine.

2. The tissue graft composition of claim 1 wherein the section of small intestine is excised from the jejunum.

3. The tissue graft composition of claim 1 formed into a cylinder having a predetermined luminal diameter and sutured along the length of the cylinder.

4. The tissue graft composition of claim 3 wherein the stratum compactum forms the luminal surface of the cylinder.

* * * * *